United States Patent
Butts

(10) Patent No.: US 6,297,047 B1
(45) Date of Patent: Oct. 2, 2001

(54) ULTRAVIOLET STERILIZATION OF $CO_2$ CELL-CULTURE INCUBATOR INTERNAL ENVIRONMENTS

(75) Inventor: Charles G. Butts, Weaverville, NC (US)

(73) Assignee: SPX Corporation, Muskegon, MI (US)

( * ) Notice: Subject to any disclaimer, the term of this patent is extended or adjusted under 35 U.S.C. 154(b) by 0 days.

(21) Appl. No.: 09/383,299

(22) Filed: Aug. 25, 1999

(51) Int. Cl.[7] .................................................. C12M 1/38
(52) U.S. Cl. ........................ 435/303.1; 435/809; 422/104; 219/400
(58) Field of Search ............................... 435/303.1, 809; 422/104; 219/400; 119/311–322; 236/2; 126/113, 508; 237/3, 4, 14

(56) References Cited

U.S. PATENT DOCUMENTS

| | | | |
|---|---|---|---|
| 3,710,791 | * | 1/1973 | Deaton .............................. 128/191 A |
| 4,936,824 | * | 6/1990 | Koch et al. ............................... 600/22 |
| 5,090,617 | * | 2/1992 | Swan et al. ................................ 236/3 |
| 5,418,131 | | 5/1995 | Butts . |
| 5,525,512 | | 6/1996 | Pieler et al. ......................... 435/303.1 |
| 5,773,287 | | 6/1998 | Binder ................................. 435/303.1 |
| 5,783,439 | | 7/1998 | Reichler et al. .................... 435/286.1 |
| 5,792,427 | | 8/1998 | Hugh et al. . |
| 5,997,397 | * | 12/1999 | Frickel et al. ........................... 454/60 |

FOREIGN PATENT DOCUMENTS 10-113096 * 5/1998 (JP) .

OTHER PUBLICATIONS

International Search Report PCT/US00/49377 (Dec.–2000).
HERAcell $CO_2$ brochure re Contra Con and BBD 6220 $CO_2$ incubators (No Date Provided).
Heraeus Instruments advertisement re $CO_2$ incubators (No Date Provided),

* cited by examiner

Primary Examiner—William H. Beisner
(74) Attorney, Agent, or Firm—Pepper Hamilton LLP

(57) ABSTRACT

A cell culture incubator (10, 72) is provided which includes one or more UV lamps (40, 116) allowing continuous or semi-continuous on-demand incubator sterilization. The incubator (10, 72) includes a thermally insulated cabinet (12, 74) having an internal working chamber (14, 76) and a hingedly mounted door (16, 78). The sterilizing UV lamp (40) may be mounted in a circulating airflow passageway (62) to continuously sterilize air circulating through the working chamber (14). Alternately or in addition thereto, the lamp (116) may be mounted in the door (78) with a reflector (114) for focusing the UV radiation into the working chamber (76). Preferably, short-wave UV lamps are employed.

11 Claims, 4 Drawing Sheets

ULTRAVIOLET STERILIZATION OF CO₂ CELL-CULTURE INCUBATOR INTERNAL ENVIRONMENTS

BACKGROUND OF THE INVENTION

1. Field of the Invention

The present invention is broadly concerned with incubators conventionally used for the incubation of cell-culture samples and which are improved by provision of an internal, continuous sterilization feature. More particularly, the invention pertains to such incubators equipped with internal ultraviolet (UV) lamps which can be user-controlled controlled to effect continuous or periodic sterilization of the internal working chambers of the incubators.

2. Description of the Prior Art

Cell culture incubators are ubiquitous in biological research laboratories. These units are designed to incubate cell culture samples, typically over a period of hours with closely controlled temperature and atmospheric conditions (e.g., 37° C. and 5% $CO_2$). Typically, incubators are in the form of an upright cabinet having an openable door and an internal working or incubating chamber equipped with a series of sample-holding shelves. Modern-day incubators normally have temperature and $CO_2$ sensors for maintaining desired internal conditions without operator intervention.

During the course of incubations, the internal working chambers of incubators can become contaminated with air borne or liquid contaminants. As a consequence, it is necessary to sterilize and decontaminate the internal working chamber and components of the incubators. Presently, such sterilization/decontamination is performed by one of two methods. In one technique, all removable components are autoclaved and non-removable components are manually wiped down with a germicidal solution. In another method, the incubator undergoes a sterilization cycle which heats the internal working chamber and its components to approximately 90° C. to kill any contaminants. Both of these prior methods are cumbersome and time-consuming. Manual decontamination requires significant labor, whereas a incubator sterilization cycle disrupts the incubator's operating temperature for several hours both during heating and the subsequent cool down period.

There is accordingly a need in the art for an improved cell culture incubator which avoids the sterilization/decontamination problems described above, and which allows continuous or intermittent sterilization/decontamination without upsetting the desired incubation conditions maintained within the working chamber of the incubator.

SUMMARY OF THE INVENTION

The present invention overcomes the problems outlined above and provides an improved incubator having an incubator cabinet presenting an internal working chamber wherein one or more ultraviolet lamps are operatively coupled with the cabinet for generating ultraviolet radiation capable of sterilizing the working chamber.

In preferred forms, the ultraviolet lamps are of the shortwave variety, generating UV radiation at about 200–280 nm. The lamps may be mounted at any convenient position within the incubator cabinet, e.g., proximal to the internal working chamber on a stationary wall thereof or on the cabinet door. The UV lamps may also be of any desired configuration such as tubular or serpentine in shape.

In one embodiment, a UV lamp is situated within an internal airflow path passing through the incubator working chamber. Thus, as incubation proceeds, the circulating air is continuously sterilized and decontaminated by the UV radiation. In another embodiment, the incubator cabinet door houses a UV lamp, and a reflector is used to direct sterilizing radiation into the incubator working chamber.

A particular advantage of the invention is that sterilization may be carried out with little or no disruption of the desired temperature and atmospheric conditions within the incubator working chamber.

DETAILED DESCRIPTION OF THE PREFERRED EMBODIMENT

Figure 1:
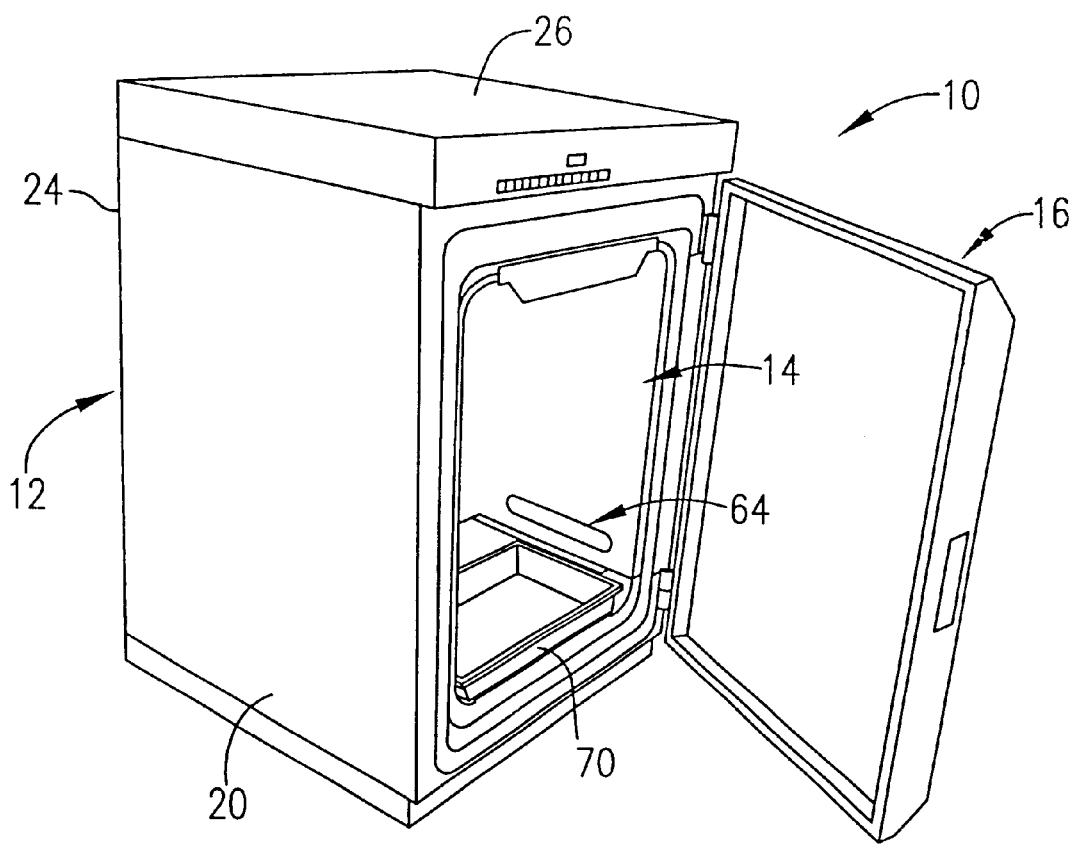
FIG. 1 is a perspective view of an incubator in accordance with the invention, shown with the shelves thereof removed.
Figure 2:
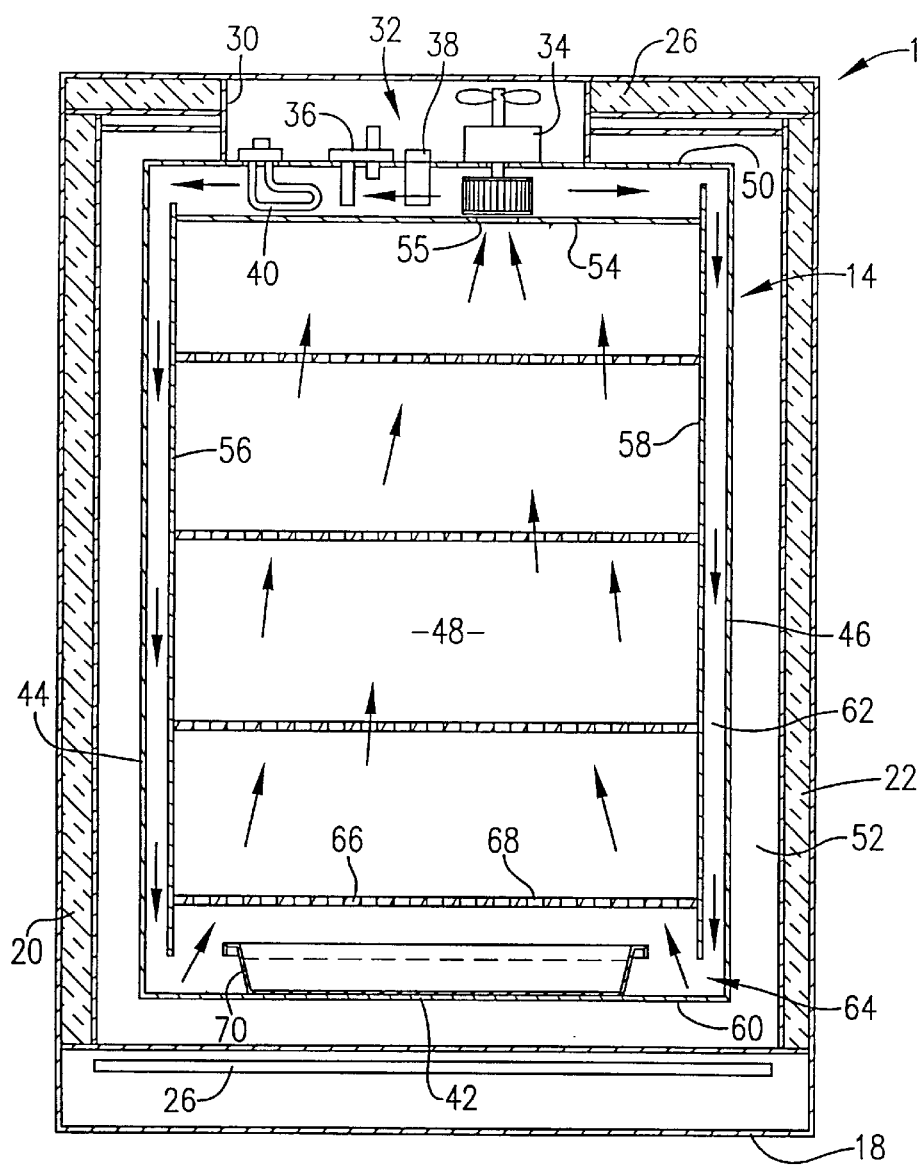
FIG. 2 is a schematic vertical sectional view of an incubator in accordance with the invention, wherein the ultraviolet sterilizing lamp of the incubator is situated within a circulating airflow path.

Turning now the drawings and particularly FIGS. 1–2, an incubator 10 in accordance with the invention is illustrated. The incubator 10 is in the form of an upright cabinet 12 equipped with an internal working chamber 14 and a door 16. The incubator 10 is adapted to receive and incubate a wide variety of biological samples.

In more detail, the cabinet 10 has a base 18, upright sidewalls 20, 22, rear wall 24 and top wall 26. The base 18 and walls 20–26 are provided with thermal insulation as illustrated. The base 18 is equipped with an electrical resistance heater 28 whereas top wall 26 includes walls 30 defining a utility space 32. The space 32 houses a blower assembly 34, temperature sensor 36, $CO_2$ sensor 38 and UV lamp 40.

The working chamber 14 is made up of interior walls, namely bottom wall 42, sidewalls 44, 46, rear wall 48 and top wall 50. The walls defining chamber 14 are located inboard of the outer cabinet walls, thus defining a surrounding plenum 52 which is adapted to receive an indirect heating medium such as air or water. Internally, the chamber 14 includes a top panel 54 apertured as at 55, depending side panels 56, 58 and bottom panel 60. It will be observed in this respect that the panels 54–58 are located inboard of the adjacent chamber walls 44–50, thereby defining an airflow passageway 62 in surrounding relationship to the panels. This passageway terminates adjacent the lower end of chamber 14 with side marginal air outlets 64. Finally, the outlet of blower assembly 34, temperature sensor 36, $CO_2$ 38 and lamp 40 are all attached to top wall 50 and extend into the air flow passageway 62.

The chamber 14 is typically provided with a series of vertically spaced shelves 66 which are perforated as at 68 to allow airflow therethrough. In addition, a water pan 70 is conventionally located atop bottom wall 42 to maintain appropriate humidity conditions within chamber 14.

In the embodiment of FIGS. 1–2, the door 16 forming a part of cabinet 12 is entirely conventional and is hingedly mounted to cabinet sidewall 22 so as to completely enclose the chamber 14 when the door is closed. To this end, conventional seals (not shown) are employed to maintain an essentially airtight condition within the working chamber 14. In the use of the embodiment of FIGS. 1–2, after appropriate temperature and $CO_2$ conditions are established (through the heating assembly and sensors 36, 38), samples to be incubated are placed on the shelves 66. As incubation proceeds, air is circulated through the working chamber 14 by the action of blower assembly 34. As shown by the air directional arrows in FIG. 2, air is directed from the blower assembly downwardly through the perforated shelves and passageway 62 where it then exits via outlets 64 and then passes upwardly through aperture 55. In this connection, the provision of temperature controller 36 and $CO_2$ sensor 38 within the passageway 62 insures that appropriate temperature and $CO_2$ conditions can be maintained within chamber 14. As those skilled in the art will appreciate, the sensor 36 is operatively coupled to the heating assembly for the incubator, and similarly the sensor 38 is used to insure constant $C0_2$ concentrations.

The provision of UV lamp 40 also insures that the incubator may be continuously or semi-continuously sterilized. Typically, a short-wave (254 nm) UV lamp is employed in this context, which provides the necessary degree of sterilization without significantly raising the internal operating temperature. The duration of the UV lamp illumination may be controlled through circuitry program with the on-time duration for a particular incubation sequence. This permits user control of the duration of illumination of the UV lamp. In order to protect the user from potentially harmful UV radiation, a safety interlock system (not shown) in the form of a door switch is provided; the switch is operable to interrupt UV radiation from lamp 40 any time the door 16 is opened.

Figure 3:
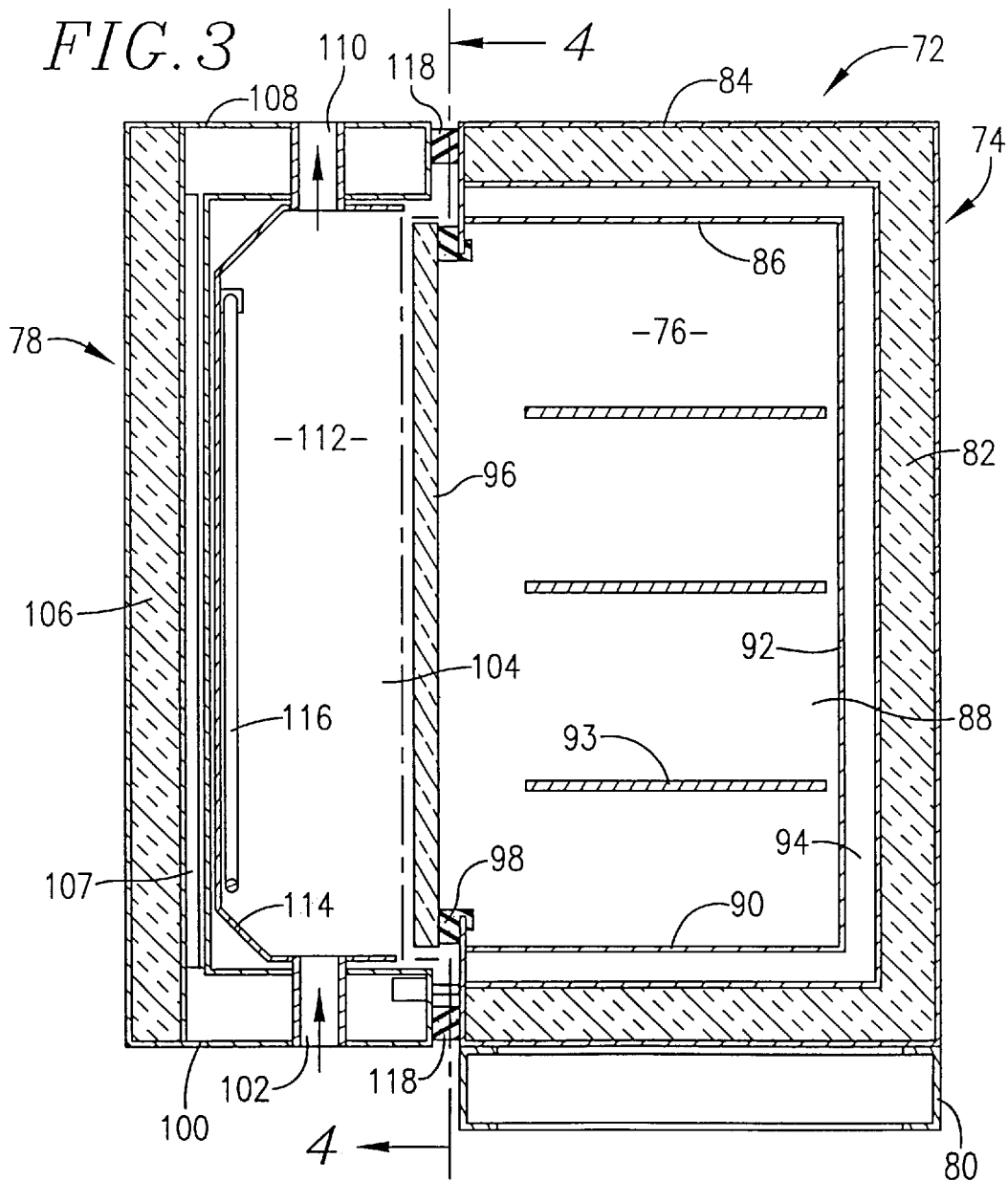
FIG. 3 is a schematic vertical sectional view of another incubator in accordance with the invention, wherein the ultraviolet lamp is mounted within the incubator cabinet door.
Figure 4:
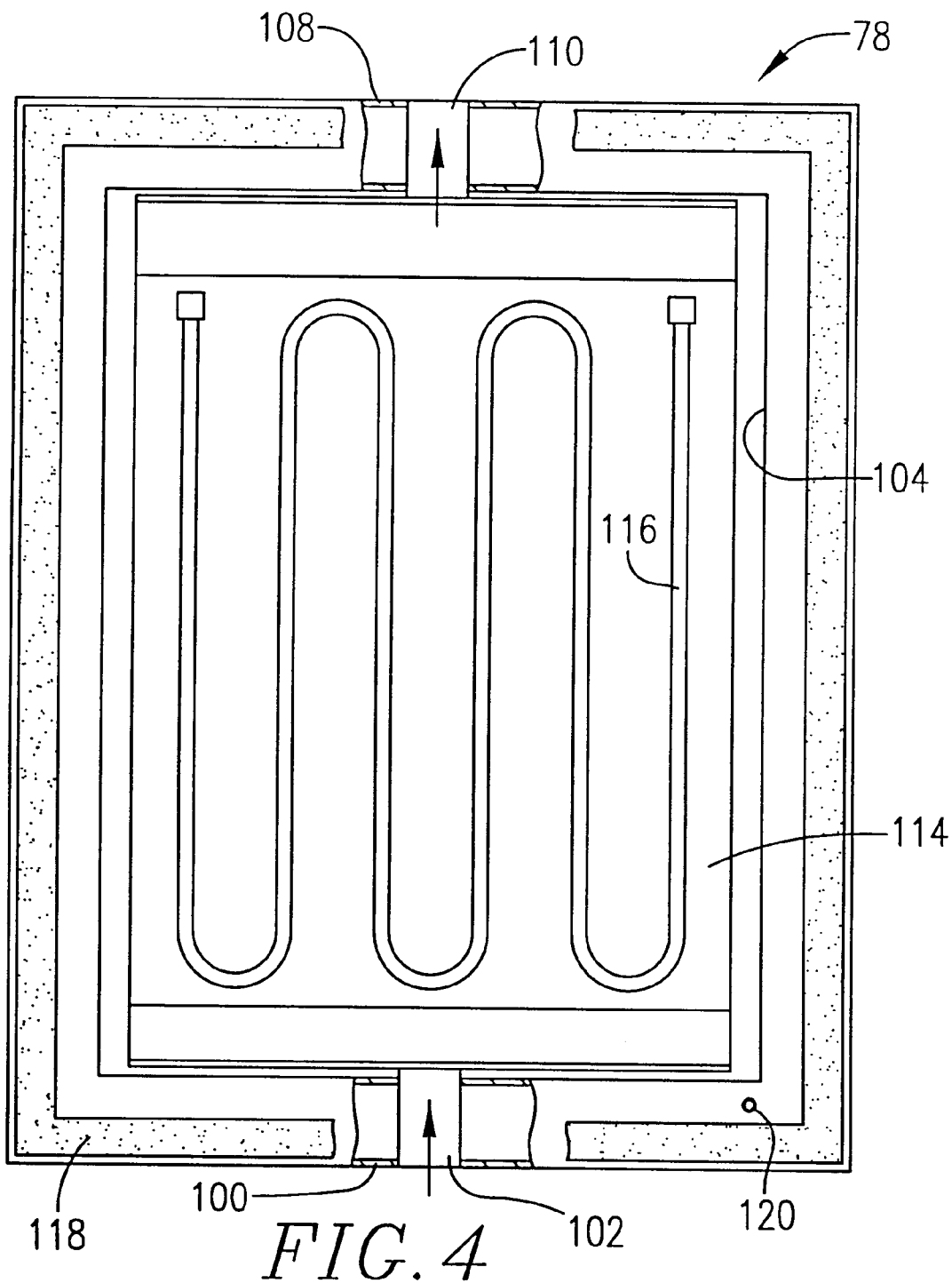
FIG. 4 is a vertical sectional view taken along line 4—4 of FIG. 3 and further depicting the configuration of the door-mounted ultraviolet lamp.

FIGS. 3–4 illustrate another incubator 72 having a controllable UV sterilization feature. In this case, the incubator 72 includes an upright cabinet 74 presenting an internal working chamber 76 and a hingedly mounted door 78. The cabinet 74 and working chamber 76 are essentially conventional, i.e., the cabinet includes a base 80, upright sidewalls, rear wall 82 and top wall 84, all of which are provided with thermal insulation. The internal working chamber 76 includes top wall 86, sidewalls 88, bottom wall 90 and rear wall 92, with vertically spaced sample-supporting shelves 93. The latter chamber-defining walls are spaced from the primary cabinet walls so as to define a plenum 94 allowing introduction of indirect heat exchange media. The cabinet 74 is also equipped with an internal transparent glass door 96 which covers the front face of working chamber 76; appropriate peripheral seals 98 are provided for maintaining a substantially airtight condition within the chamber 76.

The door 78 of cabinet 74 includes a bottom wall 100 equipped with an airflow passageway 102, upright sidewalls 104, front wall 106 supporting a resistance heater 107, and top wall 108 having airflow passageway 110 therethrough. The walls 100–106 are provided with thermal insulation. As shown, the door 78 is generally U-shaped in vertical section, thus defining an internal concave area 112. The area 112 houses a polished aluminum reflector 114 as well as a serpentine-shaped UV lamp 116 positioned adjacent and in front of the reflector 114. Marginal seals 118 extend about the inner periphery of door 78 and engage corresponding surfaces on the cabinet 74.

Although not shown in FIGS. 3–4, it will be understood that the incubator 72 has the usual internal condition control features, e.g., temperature and $CO_2$ controllers. Moreover, it also has the interlock feature of the first embodiment, namely a switch 120 associated with the door 78 so that upon opening thereof the UV lamp 116 is de-energized.

In the use of incubator 72, desired temperature and $CO_2$ conditions are established within chamber 76 and doors 78 and 96 are opened to permit placement of samples on the shelves 93. The doors are then closed and incubation proceeds in the normal fashion. As a part of the incubator procedure or thereafter, the lamp 116 (which again preferably is a short-wave 254 nm lamp) is activated. Radiation from this lamp is reflected by reflector 114 through the glass door 96, thereby sterilizing the internal working chamber 76. In order to provide the best sterilization control, the lamp 116 may be programmed for particular on-time duration(s). During such operations, air passes by convection upwardly through the passageways 102, 110 provided in the door bottom and top walls 100, 108.

Although the embodiments of FIGS. 1–2 and 3–4 have been described separately, it will be understood that a given incubator could be provided with UV sterilization lamps both as a part of the stationary cabinet structure (as in FIGS. 1–2) and as a part of the cabinet door (as in FIGS. 3–4). In addition, UV lamp(s) may be situated at different positions so long as the UV radiation is effective for sterilizing the working chamber of the incubator.

I claim:

1. An incubator comprising:

an incubator cabinet presenting an internal working chamber for incubation of samples;

an ultraviolet lamp operatively coupled with said cabinet for generating ultraviolet radiation capable of sterilizing said working chamber; and an openable door, said door being U-shaped in vertical section, thus defining an internal concave area, said ultraviolet lamp carried by said door and oriented when said door is closed for directing said ultraviolet radiation towards said working chamber.

2. The incubator of claim 1, said cabinet including a blower for circulating air along a path through said working chamber, said ultraviolet lamp located adjacent said path for sterilizing said circulating air.

3. The incubator of claim 1, said door including an inlet and an outlet spaced from the inlet for passage of circulating air through the door.

4. The incubator of claim 1, including a reflector carried by the door for reflecting ultraviolet radiation towards said working chamber.

5. The incubator of claim 1, said lamp comprising an elongated, serpentine-shaped ultraviolet lamp.

6. The incubator of claim 1, said cabinet including a heating assembly for maintaining temperature conditions within said working chamber at a desired level.

7. The incubator of claim 6, said heating assembly comprising a plenum adjacent said working chamber and adapted to receive an indirect heating medium.

8. The incubator of claim 6, said cabinet including an openable door, said heating assembly comprising a resistance heater carried by said door.

9. The incubator of claim 6, including a temperature sensor operatively coupled with said heating assembly for controlling the heating assembly in order to maintain substantially constant temperature conditions within said working chamber.

10. The incubator of claim 1, said working chamber including a plurality of spaced sample-supporting shelves.

11. The incubator of claim 10, said shelves being perforated for permitting airflow therethrough.

* * * * *